United States Patent [19]

Tatum, Jr.

[11] Patent Number: 4,511,335
[45] Date of Patent: Apr. 16, 1985

[54] DENTAL IMPLANT

[76] Inventor: O. Hilt Tatum, Jr., One Beach Dr., S.E., St. Petersburg, Fla. 33701

[21] Appl. No.: 428,920

[22] Filed: Sep. 30, 1982

[51] Int. Cl.³ .................................................. A61C 8/00
[52] U.S. Cl. ............................................. 433/173; 3/1; 3/19; 128/92 C
[58] Field of Search ............... 433/176, 172, 173, 174, 433/175

[56] References Cited

U.S. PATENT DOCUMENTS

| | | | |
|---|---|---|---|
| 3,577,853 | 5/1971 | Roberts | 433/176 |
| 3,738,004 | 6/1973 | Edelman | 433/176 |
| 3,777,402 | 12/1973 | Roberts | 433/176 |
| 3,798,771 | 3/1974 | Edelman | 433/176 |
| 3,849,888 | 11/1974 | Linkow | 433/176 |
| 3,908,269 | 9/1975 | Christenot et al. | 433/176 |
| 4,302,188 | 11/1981 | Driskell | 433/176 |
| 4,377,382 | 3/1983 | Roberts | 433/176 |

Primary Examiner—Richard J. Apley
Assistant Examiner—David Isabella
Attorney, Agent, or Firm—Frijouf, Rust & Pyle

[57] ABSTRACT

An endosseous implant is disclosed for permanent implantation within a groove formed in the posterior alveolar process in the mandible of the mouth of a patient. The implant comprises a supporting head for supporting a crown portion of an artificial tooth. The supporting head has a substantially horizontal top surface and a base portion. A constricted neck portion is rigidly secured to the base portion for supporting the supporting head. An apertured blade portion is also rigidly secured to the neck portion such that the neck portion connects together the supporting head and the blade portion. The blade portion includes a lingual and a buccal face and a mesial and a distal portion. The mesial portion of the blade portion has a blunt mesial edge and the distal portion has a distal edge of pointed configuration. The neck portion is disposed adjacent the juncture of the mesial and the distal portions and the distal portion is curved away from the longitudinal axis of the mesial portion. In use of the implant, the distal edge is inserted within a groove formed in the alveolar process and the blunt mesial edge is gently hammered so that the distal edge penetrates into the alveolar process towards the Ramus. In an alternative embodiment of the invention, the distal edge is a shallower version of the mesial portion.

12 Claims, 13 Drawing Figures

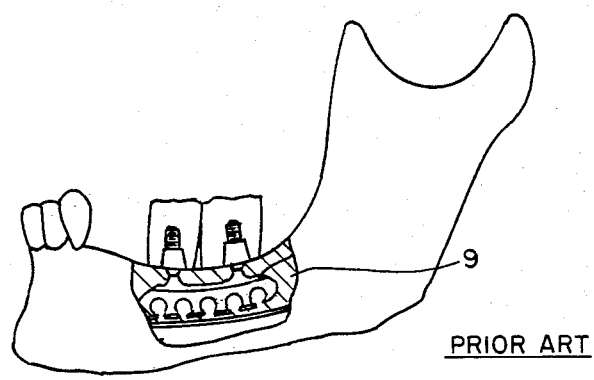
FIG. 1 PRIOR ART
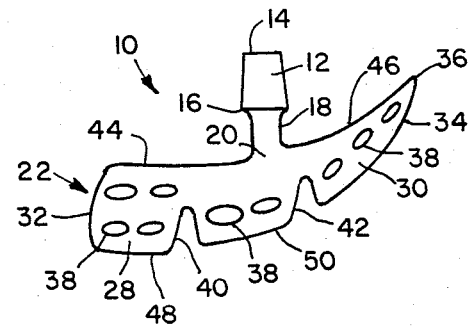
FIG. 2
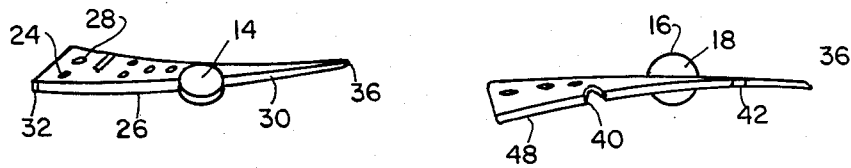
FIG. 3          FIG. 4
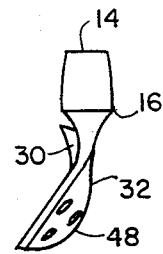  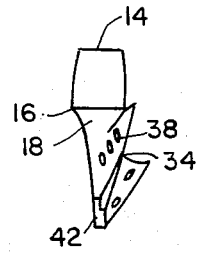
FIG. 5          FIG. 6

DENTAL IMPLANT

BACKGROUND OF THE INVENTION

1. Field of the Invention

This invention relates to an endosseous implant and more particularly to an endosseous implant of the type used for the permanent implantation within the alveolar process in the mandible of the mouth of a patient.

2. Description of the Prior Art

Implantology in the field of dentistry has gained much prominence in recent years. Originally, attempts were made regarding the transplantation of teeth. This usually necessitated the removal of a tooth from the mouth and the insertion into the vacated socket of another tooth for the same patient. This method of transplantation is known in the art as "autogeneous tooth transplantation" but suffers from various problems including root retention and the availability of a suitable transplantable tooth.

In order to overcome the aforementioned problems involved with dental transplantation, various attempts have been made over the years to provide a suitable artificial anchoring means for an artificial tooth crown. These artificial anchoring means known in the art as "subperiosteal" implants include the technique of opening up the gum, taking an impression of the jawbone and usually three to six weeks later, reopening the gum to fasten the implant adjacent the jawbone. This technique with various modifications has been practiced for over twenty-five years and has proven highly successful with the success rate running as high as 90 percent. However, the technique of subperiosteal implantation suffers from the inherent problem of requiring two surgical operations. The first operation is that of cutting open the gum in order to make an impression of the jawbone while the second operation requires the later cutting open of the gum to insert and affix the subperiostel implant to the jawbone. More recent techniques have been made to overcome the aforementioned problems associated with subperiosteal implantation. These techniques include the immediate implantation of a blade portion of an oral implant within the alveolar process or jawbone of the mouth. This latter technique is known in the art as "endosseous" implantation because the soft spongy bone of the alveolar process is penetrated by the blade portion of the oral implant. After the blade portion has been inserted into the spongy bone of the alveolar process, the spongy bone grows around the blade portion thus anchoring the oral implant firmly within the alveolar cavity vacated by the extracted tooth. The immediate advantage of the endosseous implantology technique lies in the requirement of only one surgical operation. The endosseous implant, which is provided with one or more upstanding supporting heads, is left within the insertion site usually for ten to twelve weeks while the spongy bone grows around the blade portion and then the supporting head is ready to receive a suitable crown of an artificial tooth.

Particularly with regard to the technique of endosseous implantology, U.S. Pat. No. 3,465,441 to Linkow describes a ring-type implant for artificial teeth. This specification discloses an endosseous implant having a vertical blade of open or, alternatively, ring-shaped configuration in which the lower sharp edge is driven into the patient's jawbone.

U.S. Pat. No. 3,729,325 to Linkow et al. teaches an improvement in the design of the implants of U.S. Pat. No. 3,465,441 particularly with regard to the provision of a seat at the base of the supporting head which prevents the implant from being inserted too deeply within the alveolar process.

Although FIG. 3 of U.S. Pat. No. 3,729,325 shows an endosseous implant located within a mandible, such an implant has not proved altogether satisfactory when applied to the site of posterior molars, particularly third molars. A need has existed in the art for an endosseous implant which will be anchored within the relatively massive bone structure of the Ramus.

Accordingly, the present invention has as its primary objective the provision of an endosseous implant that overcomes the aforementioned inadequacies of the prior art implants and provides implants which significantly contribute to the technique of endosseous implantology.

Another object of the present invention is the provision of an endosseous implant having a distal edge which penetrates within the Ramus.

Another object of the present invention is the provision of an endosseous implant in which a mesial portion has a blunt edge which in use of the device is gently tapped with a mallet to drive the distal edge into the Ramus.

Another object of the present invention is the provision of an endosseous implant which is driven into the site of the third molar of the mandible to provide a firmly secured anchor for an artificial third molar.

Another object of the present invention is the provision of an endosseous implant in which a distal portion of the implant is curved laterally away from the longitudinal axis of a mesial portion of the blade portion.

Another object of the present invention is the provision of an endosseous implant having a blade portion which defines top and bottom edges which edges define curves, the center of curvature of which curves are located vertically above a mesial portion of the blade portion.

Another object of the present invention is the provision of an endosseous implant having at least one indentation defined by the bottom edges of the blade portion for facilitating anchorage of the blade portion within the alveolar process.

Another object of the present invention is the provision of an endosseous implant having a distal portion which is a shallower version of the mesial portion.

The foregoing has outlined some of the pertinent objects of the present invention. These objects should be construed to be merely illustrative of some of the more prominent features and applications of the invention. Many other beneficial results can be attained by applying the disclosed invention in a different manner or modifying the invention within the scope of the disclosure. Particularly with regard to the use of the invention disclosed herein this should not be construed as limited to the application of the site of the third molars of a patient's mandible, but should include applications at other dental sites.

SUMMARY OF THE INVENTION

The endosseous implant of the present invention is defined by the appended claims with a specific embodiment shown in the attached drawing. For the purpose of summarizing the invention, the invention relates to an endosseous implant for permanent implantation within a groove formed in the posterior alveolar process of the mandible of a mouth. The invention comprises a supporting head for supporting a crown portion of an artificial tooth. The supporting head has a substantially horizontal top surface and a base portion with a constricted neck portion rigidly secured to the base portion for supporting the supporting head. An apertured blade portion is rigidly secured to the neck portion such that the neck portion connects together the supporting head relative to the blade portion. The blade portion includes a lingual face and a buccal face and a mesial portion and an adjoining distal portion. The neck portion is disposed adjacent the junction of the mesial portion with the distal portion. The mesial portion includes a substantially blunt mesial edge and the distal portion includes a distal edge of pointed configuration. The distal portion has a curvature curving away from the longitudinal axis of the mesial portion.

More particularly, the distal portion curves laterally away from the longitudinal axis of the mesial portion. The blade portion includes a bottom mesial edge, a bottom intermediate edge and a bottom distal edge. The bottom mesial edge and bottom intermediate edge define a mesial indentation therebetween with the bottom distal edge and the bottom intermediate edge defining a distal indentation therebetween. The bottom edges together define a curve having a center of curvature located substantially vertically above the mesial portion of the blade portion. The blade portion includes a mesial top surface and a distal top surface with the top surfaces defining a curve, the center of curvature of which is located substantially vertically above the mesial portion of the blade portion and the top surfaces having disposed therebetween the neck portion. The mesial and distal portions respectively of the blade portion define a plurality of apertures with each aperture extending between the lingual face and the buccal face.

The blade portion of the endosseous implant is of a configuration such that the distal edge is curved both laterally and upwardly from the longitudinal axis of the mesial portion.

The invention also relates to a method of implanting an endosseous implant within a groove formed in the alveolar process of the mandible of a mouth which includes the steps of inserting the distal edge of the distal portion of the blade portion within the groove formed in an alveolar groove of the mandible and gently hammering the blunt mesial edge with a dental mallet such that the distal knife edge penetrates into the alveolar process towards the Ramus. The gum tissue around the neck portion of the implant is then sutured. Subsequent thereto, a crown of an artificial tooth is secured to the supporting head of the implant when the bone tissue has grown around the blade portion to secure the crown relative to the mandible.

The foregoing has outlined rather broadly the more pertinent and important features of the present invention in order that the detailed description of the invention that follows may be better understood so that the present contribution to the art may be more fully appreciated. Additionally, features of the invention will be described hereinafter which form the subject of the claims of the invention. It should be appreciated by those skilled in the art that the conception and the specific embodiment disclosed may be readily utilized as a basis for modifying or designing other devices for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a fragmentary illustration of a prior art endosseous implant inserted in the lower jawbone of a patient, the bone being partially broken away and the artificial tooth structure being illustrated in broken lines;

FIG. 2 is a side view of the endosseous implant of the present invention;

FIG. 3 is a top plan view of the implant of FIG. 2;

FIG. 4 is a bottom plan view of the implant of FIG. 2;

FIG. 5 is a front end view of the implant of FIG. 2;

FIG. 6 is a rear end view of the implant of FIG. 2;

Similar reference characters refer to similar parts throughout the several views of the drawings.

DETAILED DESCRIPTION

Figure 7:
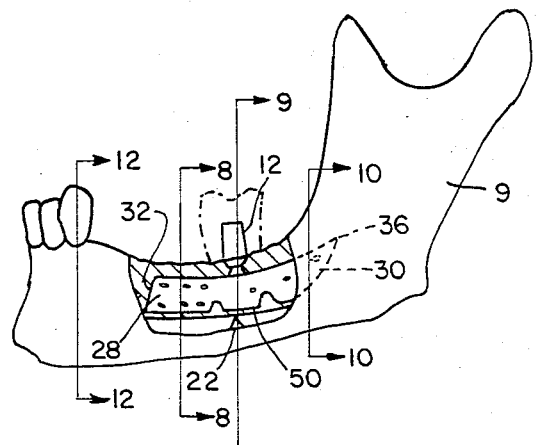
FIG. 7 is a fragmentary illustration of the endosseous implant of the present invention inserted within the mandible of a patient.
Figure 8:
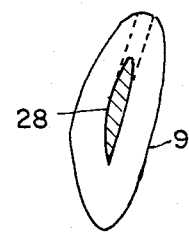
FIG. 8 is a cross-sectional view taken on the line 8—8 of FIG. 7.

FIG. 1 illustrates a prior art endosseous implant having two supporting heads and a blade portion inserted within the alveolar process of the lower jawbone or mandible 9.

FIG. 2 is a side view of the endosseous implant of the present invention generally designated 10 having a supporting head 12 which includes a substantially horizontal top surface 14 and a base portion 16. A neck portion 18 is rigidly secured to the base portion 16 of the supporting head 12. The neck is rigidly secured to an apertured blade portion 22. The blade portion 22 includes a lingual face 24 and a buccal face 26. The lingual face 24, when implanted within the jawbone of a patient faces towards the tongue while the buccal face 26 faces towards the cheek. The blade portion 22 has a mesial portion 28 and a distal portion 30 such that when implanted the mesial portion 28 is nearest to the mesial line and conversely, the distal portion 30 is farthest from the mesial line. The mesial portion 28 has a blunt mesial edge 32 and the distal portion 30 has a bottom distal edge 34 having a distal point 36. Both the mesial and distal portions 28 and 30, respectively, have a plurality of apertures 38 therein.

As shown in FIG. 1, the blade portion 22 has a bottom mesial edge 48, a bottom intermediate edge 50 and a bottom distal edge 34 such that the bottom mesial edge 48 and the bottom intermediate edge 50 define therebetween a mesial indentation 40. Similarly, the bottom distal edge 34 and the bottom intermediate edge 50 define therebetween a distal indentation 42.

The blade portion 22 also includes a mesial top edge 44 and a distal top edge 46 between which the neck portion 18 is disposed such that the neck portion 18 is rigidly secured to the blade portion 22 at the juncture 20 of the mesial portion with the distal portion.

As shown more clearly in FIGS. 5 and 6, the distal portion 30 is curved laterally away from the longitudinal axis of the mesial portion 28. With reference to FIGS. 2 to 6, the curvature of the distal portion 30 laterally away from the longitudinal axis of the mesial portion 28 is towards the lingual. However, the distal portion 30 may equally be curved laterally in the opposite direction towards the buccal.

The configuration of the blade portion 22 is such that the bottom edges 48, 50 and 34, are essentially flat as shown in FIG. 4 and define a curve having a center of curvature substantially vertically above the mesial portion 28 of the blade portion 22. Similarly, the mesial top edge 44 and distal top edge 46 define a curve such that the center of curvature is substantially vertically above the mesial portion 28 of the blade portion 22.

In use of the device, the dental surgeon makes an incision through the fibromucosal tissue at the ridge crest along the endendulous span. Tissue is then reflected away to expose alveolar bone. The cortical layer of the alveolar crest is then grooved to accomodate the implant depth. Next the distal edge 34 is inserted within the groove. A dental mallet is then used to gently tap the blunt mesial edge 32 to drive the distal edge 34 into the soft alveolar process towards the Ramus. The entire blade portion 22 is inserted within the alveolar process and the gum tissue is sutured around the upstanding neck portion 18.

Figure 12:
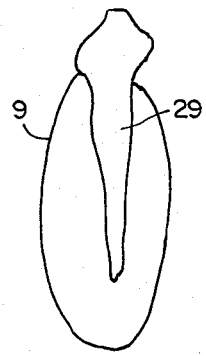
FIG. 12 is a cross-sectional view taken on the line 12—12 of FIG. 7 showing the relatively vertical disposition of a cuspid tooth.
Figure 11:
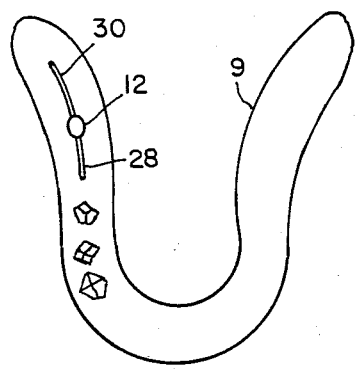
FIG. 11 is a plan view of a lower jawbone showing an implant inserted into the Ramus.

The location of the blade portion 22 is such that the mesial portion or anterior foot 28 is substantially vertical so that the portion 28 is in alignment with the cuspid 29 shown in FIG. 12. The middle portion of the blade portion 22 located between the indentations 40 and 42 includes the bottom edge 50. This middle portion is driven into the bone and follows the direction of the jawbone to lodge below the mylo-hyoid ridge to form the mylo-hyoid space. The distal portion or posterior foot 30 turns and goes laterally up the Ramus and has a more buccal flare than that of the middle portion.

Figure 9:
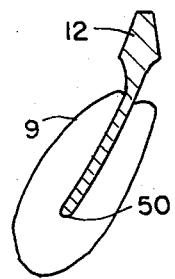
FIG. 9 is a cross-sectional view taken on the line 9—9 of FIG. 7.
Figure 10:
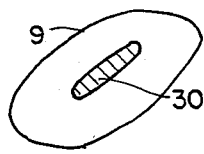
FIG. 10 is a cross-sectional view taken on the line 10—10 of FIG. 7.

As shown in FIG. 9, the supporting head 12 is curved over to the buccal in order to line up with the cuspid 9 as shown in FIG. 12.

When the endosseous implant 10 has become firmly anchored within the spongy alveolar process, usually within ten to twelve weeks, a suitable crown of an artificial tooth is secured to the supporting head 12 in a manner well known in the art.

The implants of the present invention are of three dimensional configuration and follow the natural flow of the mandible from the anterior to the posterior thereof. In order to follow the aforesaid natural flow, the blade portion is flared about the middle portion towards the buccal and then curves laterally in the region of the Ramus.

The holes 38 defined by the blade portion are oblong and increase the vertical surface area for vertical bracing relative to the jawbone.

Indentations 40 and 42 permit vertical alignment of the implant during the seating of the same into the implant socket.

Figure 13:
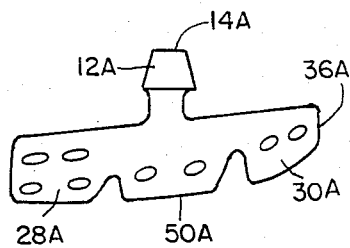
FIG. 13 is a side elevational view of an alternative embodiment of the present invention.

In an alternative embodiment of the invention as shown in FIG. 13, instead of a pointed end 36, a relatively blunt edge 36A is employed having a bottom edge for insertion into the alveolar process. In the alternative embodiment, the edge 36A is a shallower version of the mesial portion 28.

The endosseous implant of the present invention is of titanium, although various chrome cobalt alloys could be used. The dimensions of the implant will vary according to the size of the jawbone and the implant may be manufactured to the required size, but typically will measure 1⅜" from the mesial edge to the distal point.

An important feature of the present invention is the provision of an endosseous implant having a distal edge which penetrates into the alveolar process towards the Ramus and a blunt mesial edge to facilitate the tapping of the distal edge into the required location.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An endosseous implant for permanent implantation within a groove formed in the posterior alveolar process of of the mandible of a patient's mouth, comprising in combination:
   a supporting head for supporting a crown portion of an artificial tooth, said supporting head having a base portion;
   a constricted neck portion disposed adjacent to said base portion for supporting said supported head;
   an apertured blade portion disposed adjacent to said neck portion such that said neck portion connects together said supporting head relative to said blade portion;
   said blade portion including a lingual face and buccal face;
   said blade portion including a mesial portion and an adjoining distal portion;
   said neck portion being disposed adjacent the juncture of said mesial portion with said distal portion;
   said mesial portion including a substantially blunt mesial edge;
   said distal portion including a distal edge of pointed configuration; and
   said distal portion defining a curvature which curves in a lateral medial plane, said distal portion additionally being twisted about the longitudinal axis of said mesial portion for yielding a three dimensional configuration such that the implant follows the natural flow of the mandible towards the Ramus.

2. An endosseous implant as set forth in claim 1, wherein said blade portion includes a bottom mesial edge, a bottom intermediate edge, and a bottom distal edge.

3. An endosseous implant as set forth in claim 2, wherein said blade portion defines a mesial indentation disposed between said bottom mesial edge and said bottom intermediate edge.

4. An endosseous implant as set forth in claim 2, wherein said blade portion defines a distal indentation disposed between said bottom intermediate edge and said bottom distal edge.

5. An endosseous implant as set forth in claim 2, wherein said blade portion defines a mesial indentation and a distal indentation, said mesial indentation being disposed between said bottom mesial edge and said bottom intermediate edge, said distal indentation being disposed between said bottom intermediate edge and said bottom distal edge.

6. An endosseous implant as set forth in claim 2, wherein said bottom mesial edge, said bottom intermediate edge and said bottom distal edge together define a curve having a center of curvature located substantially vertically above said mesial portion.

7. An endosseous implant as set forth in claim 1 wherein said blade portion includes a mesial top surface and a distal top surface.

8. An endosseous implant as set forth in claim 7, wherein said mesial top surface and said distal top surface together define a curve having a center of curvature located substantially vertically above said mesial portion.

9. An endosseous implant as set forth in claim 7, wherein said neck portion is disposed between said mesial top surface and said distal top surface.

10. An endosseous implant as set forth in claim 1, wherein said mesial portion and said distal portion of said blade portion define respectively a plurality of apertures, each of said apertures extending between said lingual face and said buccal face.

11. An endosseous implant for permanent implantation within a groove formed in the alveolar process of the mandible of a patient comprising in combination:
a supporting head for supporting a crown portion of an artificial tooth, said supporting head including a base portion;
a constricted neck portion disposed adjacent to said base portion for supporting said supporting head;
an aperture blade portion disposed adjacent to said neck portion for connecting together and supporting said head and said blade portion;
said blade portion including a mesial portion having a blunt mesial edge;
a distal portion having a distal edge;
a lingual face;
a buccal face; and
said blade portion being of a configuration such that said distal knife edge is curved both laterally and upwardly away from the longitudinal axis of the mesial portion, said distal portion additionally being twisted about the longitudinal axis of said mesial portion for yielding a three dimensional configuration such that the implant follows the natural flow of the mandible towards the Ramus.

12. A method of implanting an endosseous implant having a blade being of a configuration such that a distal knife edge is curved both laterally and upwardly away from the longitudinal axis of a mesial portion, said distal portion additionally being twisted about the longitudinal axis of said mesial portion thereby yielding a three dimensional configuration such that the implant follows the natural flow of the mandible towards the Ramus within a groove formed in the alveolar process of the mandible of a mouth including the steps of:
inserting the distal edge of the distal portion of the blade portion within the groove formed in an alveolar groove of the mandible;
gently hammering the blunt mesial edge with a dental mallet such that the distal edge penetrates into the alveolar process and the three dimensional configuration of the distal portion follows the natural flow of the mandible towards the Ramus from the anterior to to the posterior thereof;
suturing the gum tissue around the neck portion of the implant; and
securing a crown of an artificial tooth to the supporting head of the implant when the bone tissue has grown around the blade portion to secure the same within the mandible.

* * * * *